United States Patent [19]

John, Jr. et al.

[11] Patent Number: 5,088,328
[45] Date of Patent: Feb. 18, 1992

[54] RAPID CHANGEOVER MULTI-DIAMETER ULTRASONIC TUBE INSPECTION SYSTEM

[75] Inventors: Clarence D. John, Jr., Penns Hills Twp., Allegheny County; Richard S. Wengewicz, Murrysville, both of Pa.

[73] Assignee: Westinghouse Electric Corp., Pittsburgh, Pa.

[21] Appl. No.: 555,866

[22] Filed: Jul. 20, 1990

[51] Int. Cl.$^5$ .............................................. G01N 9/24
[52] U.S. Cl. ....................................... 73/622; 73/627; 73/628
[58] Field of Search ................. 73/622, 627, 637, 638, 73/640, 626, 628

[56] References Cited

U.S. PATENT DOCUMENTS

| | | | |
|---|---|---|---|
| 3,289,468 | 12/1966 | Van Der Veer et al. | 73/637 |
| 3,375,706 | 4/1968 | Pandelis et al. | 73/622 |
| 3,415,111 | 12/1968 | Chattaway et al. | 73/641 |
| 3,455,150 | 7/1969 | Wood | 73/640 |
| 3,678,735 | 7/1972 | Boulanger et al. | 73/641 |
| 3,828,609 | 8/1974 | Furon et al. | 73/67.8 S |
| 4,554,128 | 11/1985 | Parker et al. | 376/252 |
| 4,597,294 | 7/1986 | Brill, III et al. | 73/623 |
| 4,689,193 | 8/1987 | van Swam et al. | 376/251 |
| 4,735,541 | 4/1988 | John, Jr. | 414/401 |

FOREIGN PATENT DOCUMENTS

| | | | |
|---|---|---|---|
| 0081747 | 6/1983 | European Pat. Off. | |
| 0213861 | 10/1985 | Japan | 73/579 |
| 0563620 | 6/1977 | U.S.S.R. | 73/622 |

OTHER PUBLICATIONS

Nuclear Engineering International, Feb. 1986, pp. 46-47, "KWU Offer a Mobile Reconstitution Unit for PWR Fuel".

Primary Examiner—Hezron E. Williams
Assistant Examiner—Rose M. Finley
Attorney, Agent, or Firm—Joseph C. Spadacene

[57] ABSTRACT

An ultrasonic tube inspection system capable of rapid changeover for inspecting tubes of different diameter sizes includes a serial arrangement of multiple separate inspection stations. One inspection station is used to inspect for tube dimensions irrespective of the tube diameter size. The other inspection stations are used to inspect for flaws and are employed for different ones of the tube diameter sizes to be inspected. A set of ultrasonic transducer assemblies is supported at each inspection station. The transducer assemblies at the flaw inspection stations are in proper orientations corresponding to the diameter sizes of the particular tubes to be inspected at the respective inspection stations without the need for readjustment. The inspection stations contain quantities of liquid for coupling ultrasonic energy between the ultrasonic transducer assemblies and the tube passing through the inspection stations. Liquid level control stations are disposed at opposite ends of the serial arrangement of inspection stations and are connected in flow communication with the inspection stations for controlling liquid level in the inspection stations. Tube drive are disposed adjacent the liquid level control stations and are operable to drive the tubes through the control and inspection stations such that the tubes are aligned along a common centerline irrespective of which tube diameter size is being inspected.

25 Claims, 13 Drawing Sheets

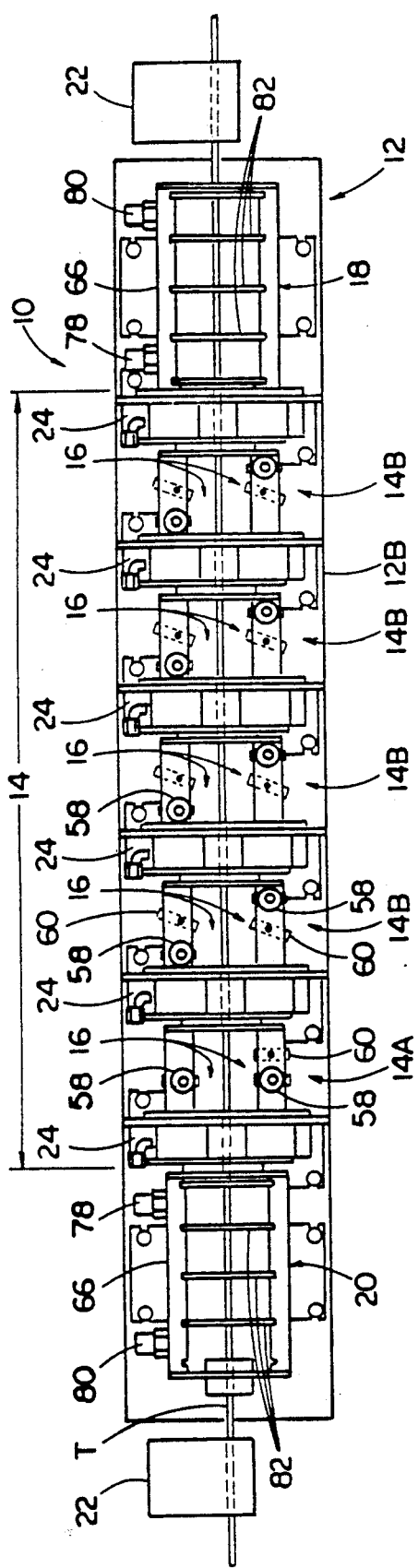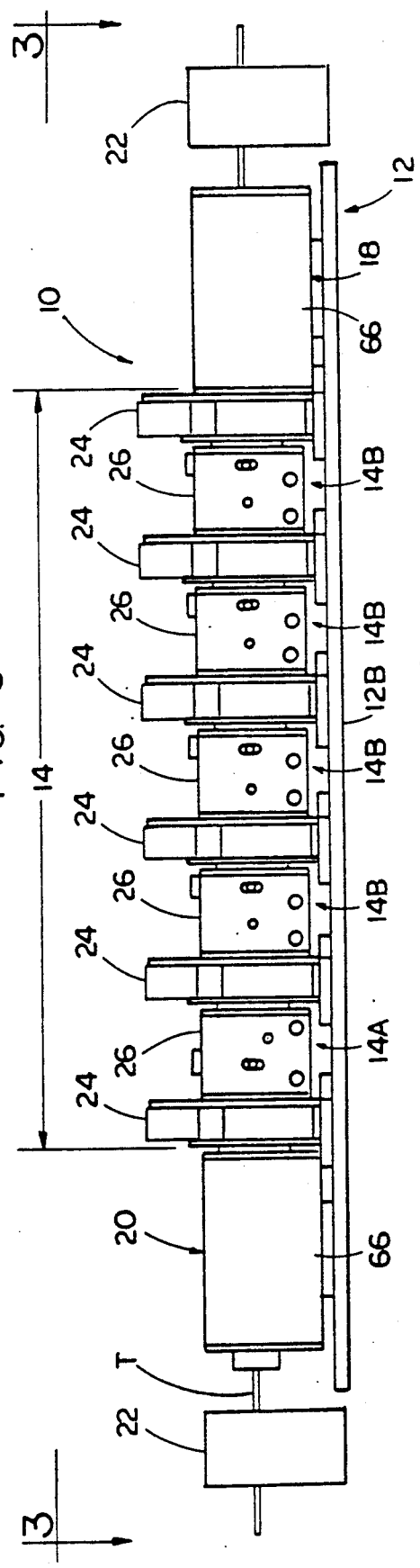

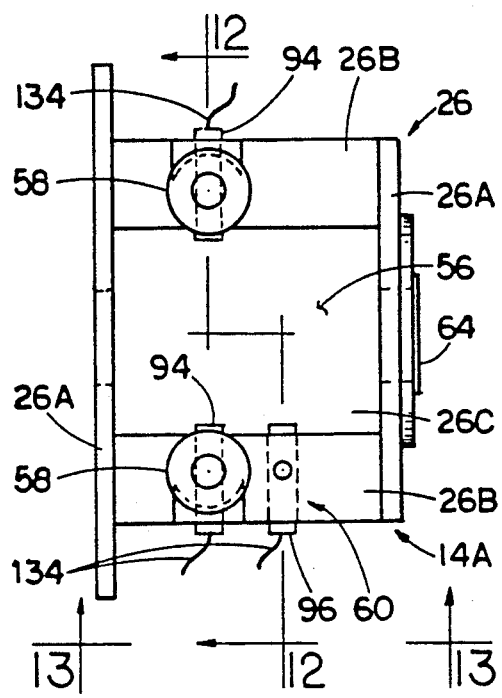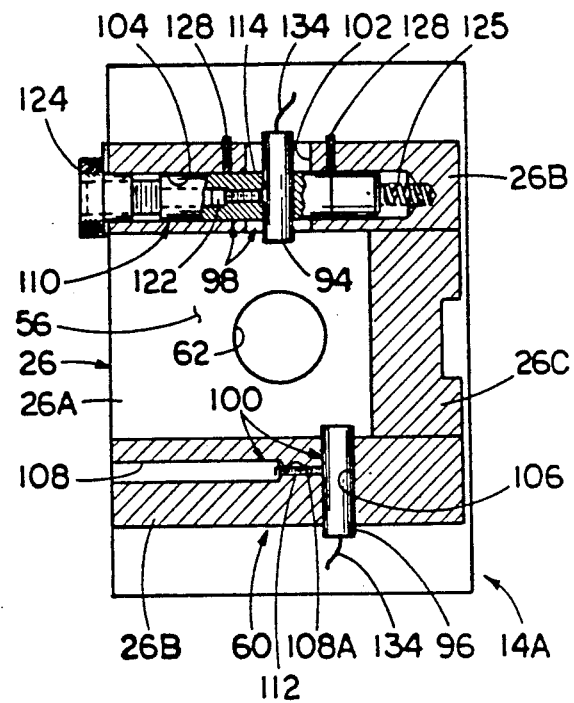
FIG 11    FIG 12
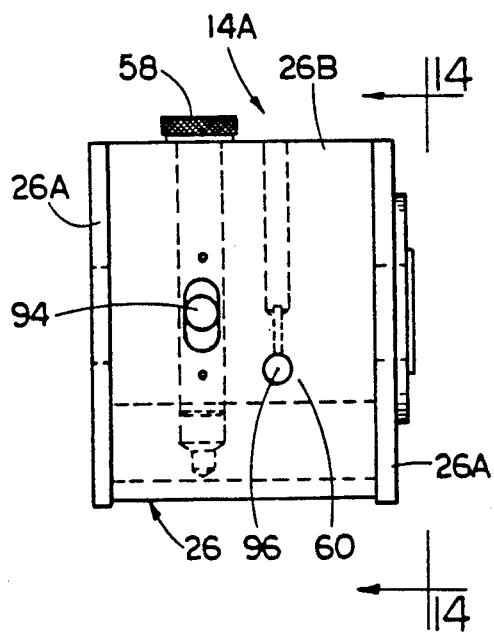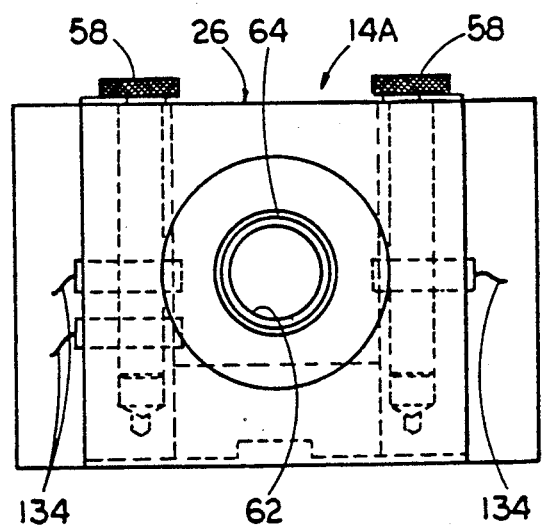
FIG 13    FIG 14

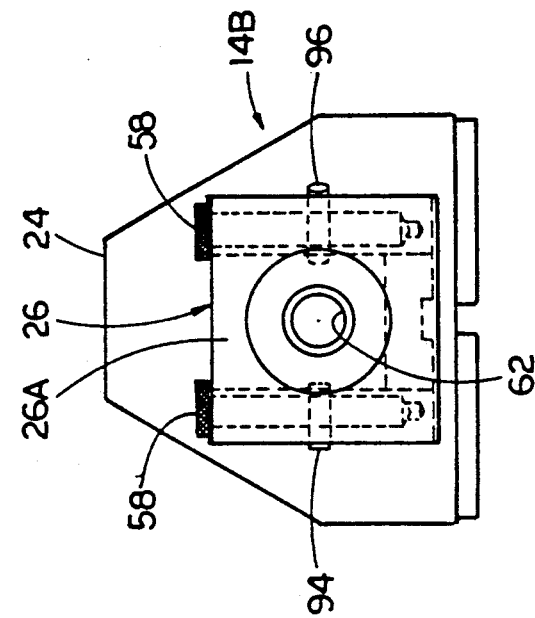
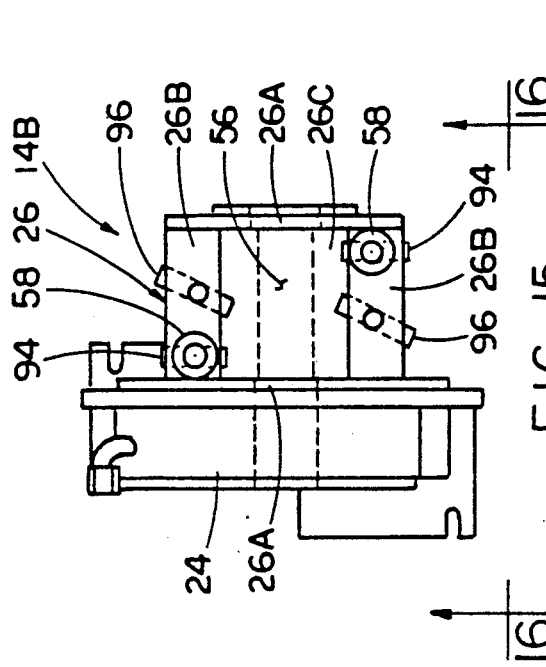
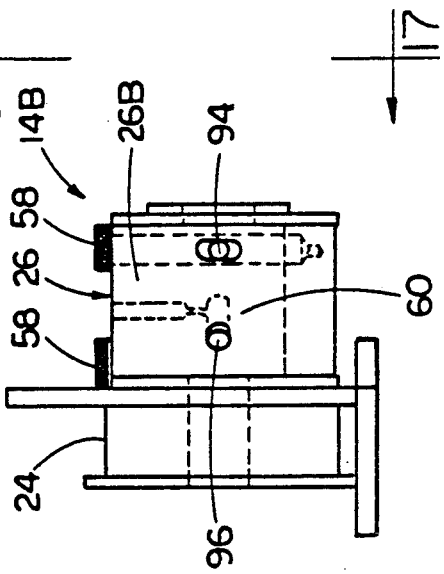

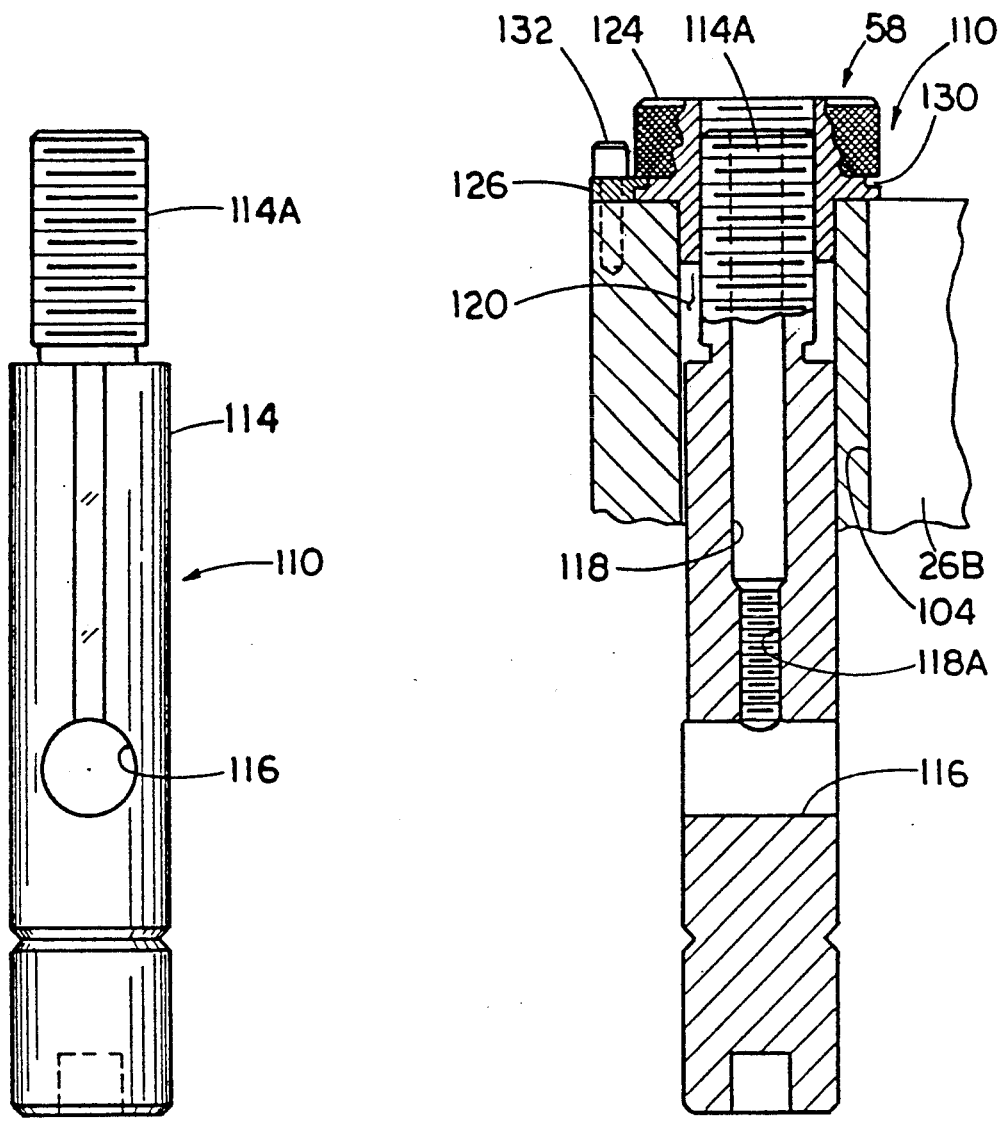
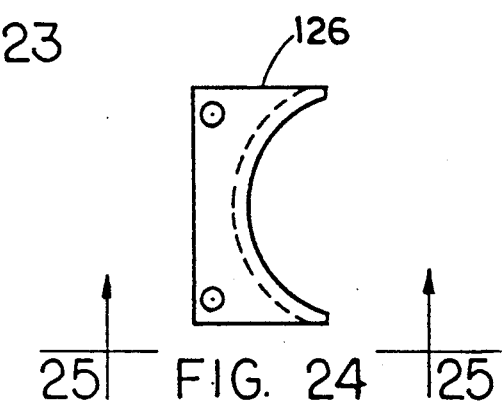
FIG. 23  FIG. 22
FIG. 24
FIG. 25

RAPID CHANGEOVER MULTI-DIAMETER ULTRASONIC TUBE INSPECTION SYSTEM

CROSS REFERENCE TO RELATED APPLICATION

Reference is hereby made to the following copending patent application assigned to the same assignee as the present invention: "Ultrasonic Tube Inspection Station For A Rapid Changeover Multi-Diameter Tube Inspection System" by Clarence D. John, Jr. et al, assigned U.S. Ser. No. 555,347 and filed July 20, 1990.

BACKGROUND OF THE INVENTION

1. Field of the Invention

The present invention relates generally to tube quality inspection, and more particularly, to an ultrasonic tube inspection system capable of rapid changeover for inspecting tubes of different diameters.

2. Description of the Prior Art

Because of their critical roles in fuel, control and instrumentation rods in nuclear reactors, tubes composed of zirconium and other materials must meet very stringent quality control standards. Parameters of interest are typically outside diameter, inside diameter, and wall thickness of the tube and material flaws in the tube. Ultrasonic inspection is one common method used to identify unacceptable dimensional deviations and material flaws in the tube.

These parameters of the tube are measured by ultrasonic transducers which send out ultrasound waves, pick up the echo of such waves and transform it into voltage signals which are recorded on a strip chart and visually tracked on a display, such as a cathode ray tube. These transducers, located in tanks filled with water, read the tube dimensions and flaws as a drive system feeds the tube through the tank. One conventional ultrasonic tube inspection system is disclosed in U.S. Pat. No. 3,828,609 to Furon et al. One conventional tube drive apparatus is disclosed in U.S. Pat. No. 4,735,541 to Clarence D. John, Jr. which is assigned to the assignee of the present invention.

The problem with conventional ultrasonic tube inspection systems is that in order to inspect tubes of different diameter sizes the orientation of the transducers in the tank must be changed, possibly every few hours or every week, depending on the need. The changeover time for converting the system to handle a different tube diameter size may typically take from four to eight hours.

Consequently, a need exists for improvements in ultrasonic tube inspection systems which will avoid the necessity to perform the time-consuming modifications previously required in order to inspect different sized tubes.

SUMMARY OF THE INVENTION

The present invention provides a rapid changeover multi-diameter ultrasonic tube inspection system designed to satisfy the aforementioned needs. The modifications necessary for changing over to inspect different tube diameter sizes are few in number and can take as little as a few minutes and at most less than one hour to complete. The unique approach of the present invention is to provide an ultrasonic tube inspection system incorporating a serial arrangement of multiple separate inspection stations corresponding to different tube diameter sizes to be inspected. The ultrasonic transducer assemblies are constantly supported in the proper orientation at the respective inspection stations without the need for readjustment to match the different sizes of the tube diameter. The same tube support stands and tube drives are used and keep the tubes aligned along a common centerline irrespective of which tube diameter size is being inspected.

Accordingly, the present invention relates to an ultrasonic tube inspection system capable of rapid changeover for inspecting tubes of different diameter sizes. The ultrasonic tube inspection system comprises a serial arrangement of multiple separate inspection stations corresponding to different tube diameter sizes to be inspected and containing an energy coupling liquid, and tube parameter measuring means supported at each of the stations in a proper orientation corresponding to the diameter size of the particular tube to be inspected at the respective station without the need for readjustment. The inspection system also includes entry and exit liquid level control stations disposed at opposite ends of the serial arrangement of inspection stations for controlling the level of energy coupling liquid in the inspection stations. The system further includes tube drives disposed adjacent to the liquid level control stations at respective opposite ends of the serial arrangement of inspection stations for driving tubes through the inspection stations and liquid level control stations while aligned along a common centerline irrespective of which tube diameter size is being inspected. One of the inspection stations is a tube dimension inspection station which is employed with the tubes irrespective of their diameter sizes, whereas the other inspection stations are tube flaw inspection stations with each employed with only one of the different tube diameter sizes.

More particularly, each inspection station includes a receptacle and a tube guiding means. Each receptacle defines a cavity for holding a quantity of energy coupling liquid and mounts the tube parameter measuring means, preferably, being ultrasonic transducer assemblies. Also, each receptacle has a pair of opposite openings to the cavity for receiving and passing a tube therethrough such that the parameters of the tube can be measured by the transducer assemblies as the tube passes through the receptacle cavity.

Further, each tube guiding means includes a housing having a central passage for receiving and passing a tube therethrough and a self-centering mechanism mounted in the housing and aligned with the passage for guiding the tube through the passage and through the receptacle cavity and openings along the common centerline irrespective of which tube diameter size is being inspected. The cavities of the receptacles are interconnected in liquid flow relationship with one another by means of the openings of the receptacles and the central passages of the tube guiding means. Also, each tube guiding means supports the one of the receptacles disposed at the same inspection station.

Each entry and exit liquid level control station disposed at the respective opposite ends of the serial arrangement of inspection stations includes a pair of tanks and a liquid level regulating arrangement coupled to each tank for controlling the level of liquid in each tank and thereby in the receptacle cavities of the inspection stations. Each tank is disposed at one of the opposite ends of the serial arrangement of inspection stations and interconnected in fluid flow communication with the one opposite end. Also, each tank has a chamber for holding liquid and a pair of opposite inlet and outlet openings to the chamber to permit passage of the tube through the chamber. Each liquid level regulating arrangement includes a plurality of dam and guide assemblies mounted in a respective tank and liquid inlet and outlet orifices on the tank which communicate with the tank cavity. Each dam and guide assembly is composed of a dam member having an upper liquid overflow portion and of a tube guide member mounted to a central opening of the dam member.

These and other features and advantages of the present invention will become apparent to those skilled in the art upon a reading of the following detailed description when taken in conjunction with the drawings wherein there is shown and described illustrative embodiments of the invention.

BRIEF DESCRIPTION OF THE DRAWINGS

In the course of the following detailed description, reference will be made to the attached drawings in which:

FIG. 2 is an enlarged fragmentary side elevational view of the tube inspection system of FIG. 1.

FIG. 3 is a top plan view of the tube inspection system as seen along line 3—3 of FIG. 2.

FIG. 11 is an enlarged top plan view of a receptacle and an arrangement of ultrasonic transducer assemblies of the tube dimension inspection station of FIG. 8.

FIG. 12 is a cross sectional view of the receptacle and arrangement of transducer assemblies taken along line 12—12 of FIG. 11.

FIG. 13 is a side elevational view of the receptacle and arrangement of transducer assemblies as seen along line 13—13 of FIG. 11.

FIG. 14 is an end elevational view of the receptacle and arrangement of transducer assemblies as long line 14—14 of FIG. 13.

FIG. 15 is an enlarged top plan view of one of the tube flaw inspection stations of the tube inspection system of FIG. 3 in accordance with the invention of the cross-reference application.

FIG. 16 is a side elevational view of the tube flaw inspection station as seen along line 16—16 of FIG. 15.

FIG. 17 is an end elevational view of the tube flaw inspection station as seen along 17—17 of FIG. 16.

FIG. 22 is an enlarged fragmentary sectional view of the receptacle and one of the longitudinal flaw transducer assemblies of the arrangement of transducer assemblies of FIG. 19.

FIG. 23 is an enlarged side elevational view of a transducer mounting cylinder of the longitudinal flaw transducer assembly of FIG. 22 removed from the assembly.

FIG. 24 is an enlarged plan view of a retainer plate of the longitudinal flaw transducer assembly of FIG. 22 removed from the assembly.

FIG. 25 is an end view of the retainer plate as seen along line 25—25 of FIG. 24.

DESCRIPTION OF THE PREFERRED EMBODIMENTS

Figure 1:
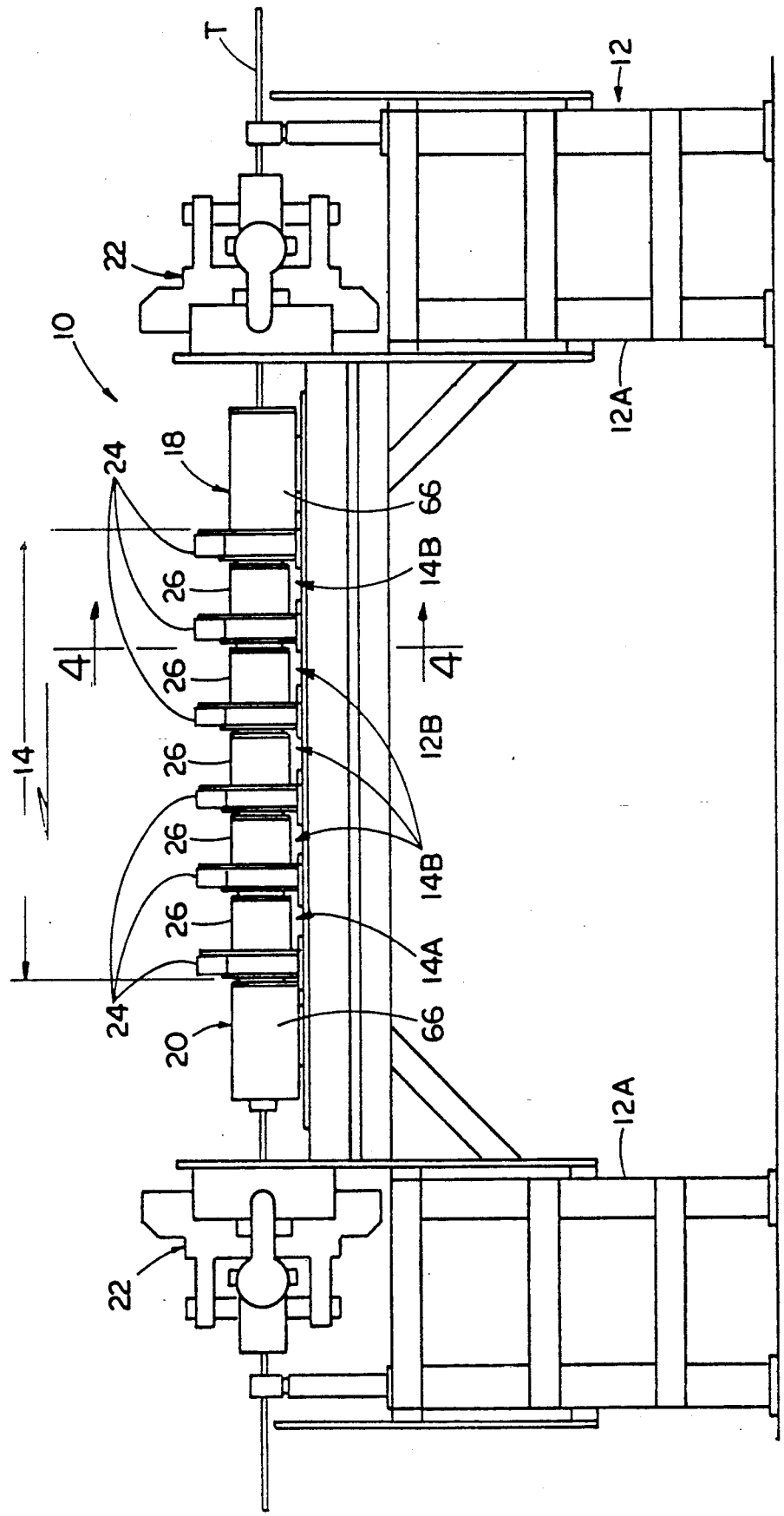
FIG. 1 is a side elevational view of an ultrasonic tube inspection system in accordance with the present invention.
Figure 5:
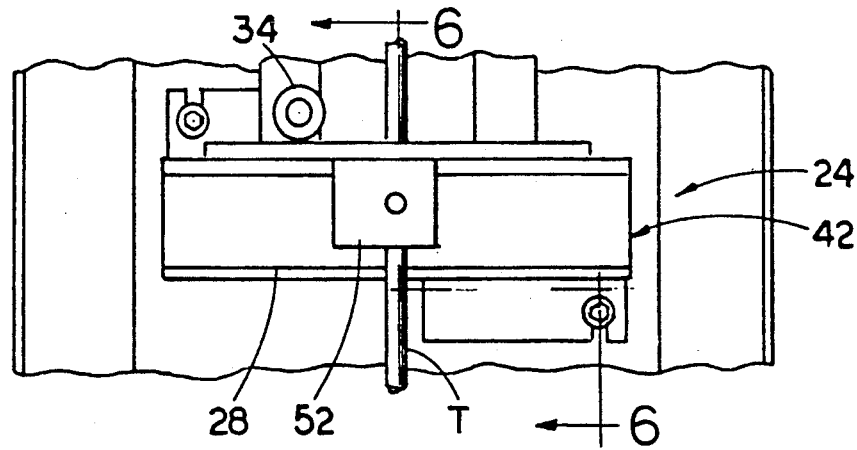
FIG. 5 is a top plan view of the tube guide stand as seen along line 5—5 of FIG. 4.

In the following description, like reference characters designate like or corresponding parts throughout the several views of the drawings. Also in the following description, it is to be understood that such terms as "forward", "rearward", "left", "right", "upwardly", "downwardly", and the like are words of convenience and are not to be construed as limiting terms.

In General

Referring to the drawings, and particularly to FIGS. 1 to 3, there is shown a rapid changeover multi-diameter tube inspection system, generally designated 10, constructed in accordance with the principles of the present invention. The multi-diameter tube inspection system 10 can be used to ultrasonically inspect tubes of different diameter sizes intended to be employed in many different uses. One particular application of interest is the inspection of tubes T to be used in fuel, instrumentation, and control rods of a nuclear fuel assembly.

In its basic components, the multi-diameter tube inspection system 10 includes a support framework 12, a serial arrangement 14 of multiple separate inspection stations 14A, 14B, tube parameter measuring means 16, entry and exit liquid level control stations 18, 20 and tube drives 22. The support framework 12 of the inspection system 10 includes a pair of spaced apart upright opposite end frame portions 12A and a middle frame portion 12B extending horizontally between and interconnecting the end frame portions 12A. The horizontal middle frame portion 12B supports the serial arrangement 14 of inspection stations 14A, 14B and the entry and exit liquid level control stations 18 and 20. The opposite end frame portions 12A respectively support the tube drives 22 adjacent the respective liquid level control stations 18, 20 at the opposite ends of the serial arrangement 14 of inspection stations 14A, 14B.

The separate inspection stations 14A, 14B in the serial arrangement 14 thereof correspond to the tube dimensions and different tube diameter sizes to be inspected. In particular, the stations are composed of a single tube dimension station 14A and a plurality of tube flaw inspection stations 14B.

Serial Arrangement of Separate Inspection Stations

Referring to FIGS. 1 to 21, each of the inspection stations 14A, 14B in the serial arrangement 14 thereof includes a tube guide stand 24 and a receptacle 26. As best seen in FIGS. 4 to 7, the tube guide stand 24 includes a housing 28 which supports from one end thereof the one receptacle 26 of the same respective inspection station. The housing 28 has a base 30 slidably mounted to the horizontal middle frame portion 12B by a dovetail interconnection 32. The housing 28 and receptacle 26 therewith can be slidably moved to a desired position along the frame portion 12B via the dovetail interconnection 32 and then anchored at such position by tightening a plurality of fasteners 34. A centering rod 36 attached to the housing base 30 slides in a complementary recess 38 formed in the middle frame portion 12B to maintain all of the tube guide stands 24 in alignment so as to define a common centerline C.

Figure 4:
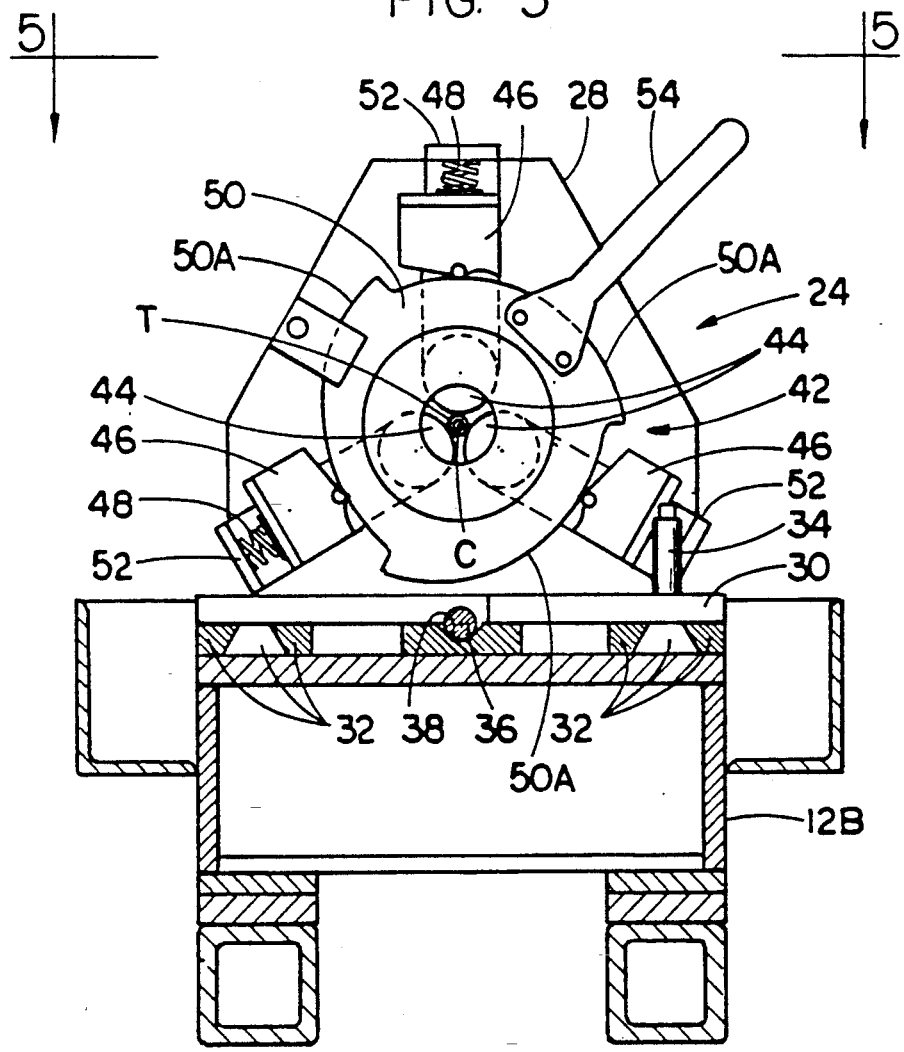
FIG. 4 is an enlarged end elevational view of one of the tube guide stands of the tube inspection system taken along line 4—4 of FIG. 1.
Figures 6, 7:
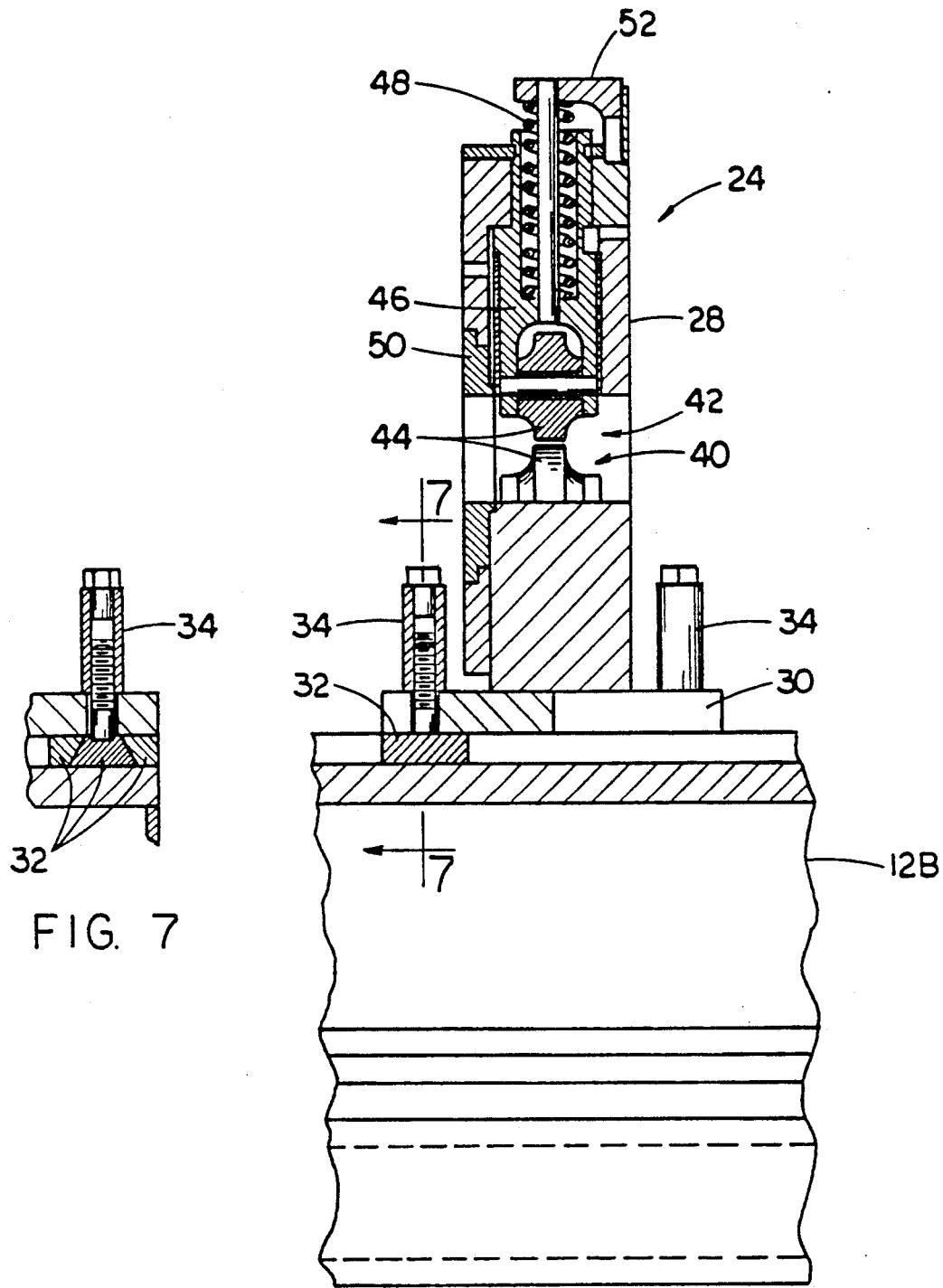
FIG. 6 is a cross-sectional view of the tube guide stand taken along line 6—6 of FIG. 5.
FIG. 7 is a fragmentary axial sectional view taken along line 7—7 of FIG. 6.
Figure 10:
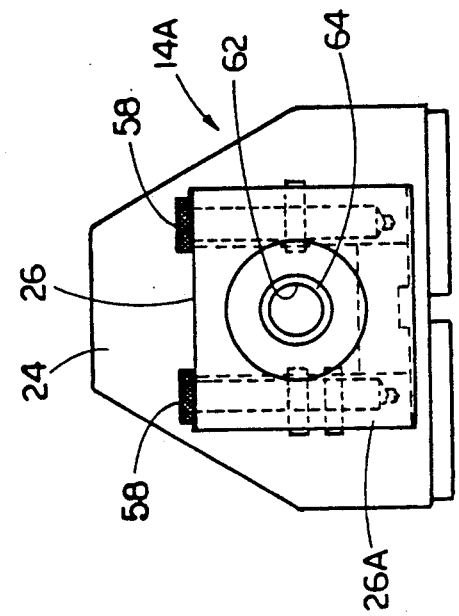
FIG. 10 is an end elevational view of the tube dimension inspection station as seen along 10—10 of FIG. 9.
Figure 8:
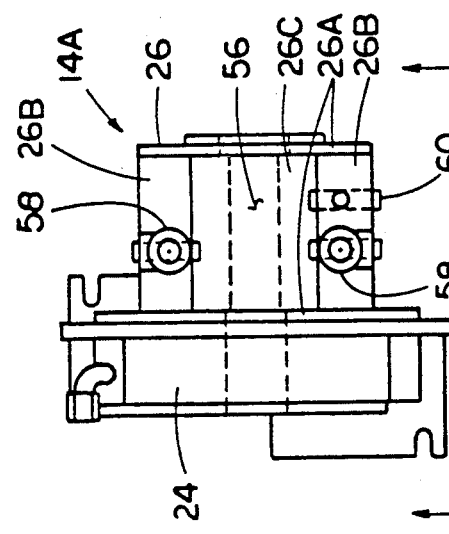
FIG. 8 is an enlarged top plan view of the tube dimension inspection station of the tube inspection system of FIG. 3 in accordance with the invention of the cross-referenced application.
Figure 9:
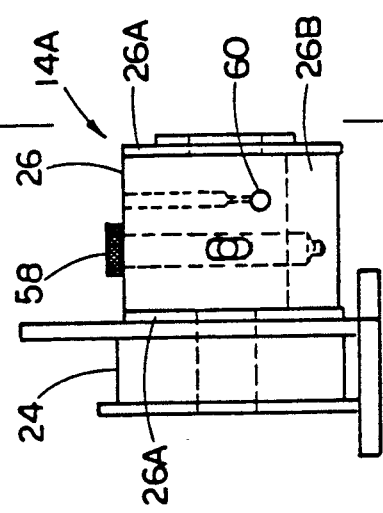
FIG. 9 is a side elevational view of the tube dimension inspection station as seen along line 9—9 of FIG. 8.
Figure 18:
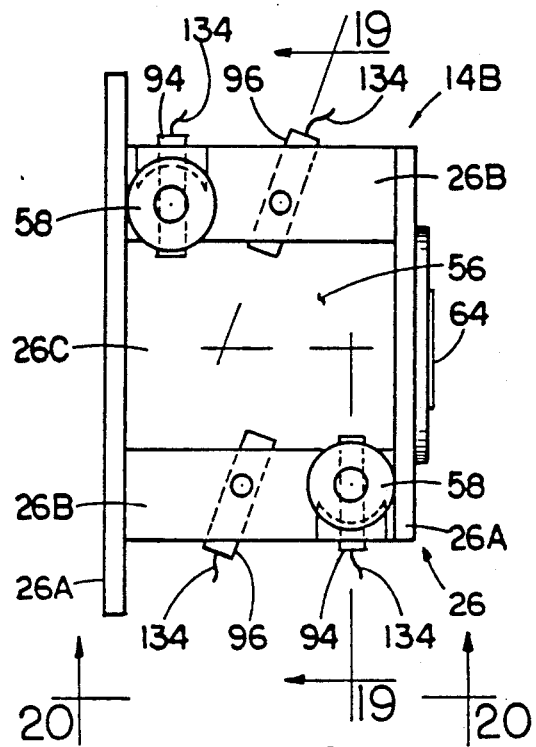
FIG. 18 is an enlarged top plan view of a receptacle and an arrangement of ultrasonic transducer assemblies of the tube flaw inspection station of FIG. 15.

As best seen in FIGS. 4 and 6, each housing 28 has a central passage 40 for receiving and passing a tube T therethrough. A self-centering mechanism 42 is mounted on the housing 27 and aligned with the passage 40. The self-centering mechanism 42 is operable for guiding the tube T through the passage 40 along the common centerline C irrespective of which tube diameter size is being inspected. Thus, together the self-centering mechanisms 42 of the aligned tube guide stands 24 ensure that each tube T is guided through the inspection stations 14A, 14B centered coaxially along the common centerline C.

More particularly, the self-centering mechanism 42 includes a plurality of tube support elements in the form of rollers 44, a plurality of arms 46 mounted to the housing 28 for movement in a reciprocal radial relation to the common centerline C and mounted in spaced relation to one another circumferentially about the common centerline C. Each arm 46 mounts one of the tube support rollers 44 at its inner end such that the rollers 44 are arranged in spaced circumferential relation about the tube T for maintaining the tube aligned along and coaxially with the common centerline C.

The self-centering mechanism 42 also includes positioning means in the form of a plurality of biasing springs 48 and a disk- or plate-like actuating cam 50. Each biasing spring 48 is mounted between a stationary bracket 52 attached to the housing 28 and an outer end of one of the arms 46 and acts to bias the arm to move radially inwardly toward the common centerline C so as to maintain the tube support rollers 44 in engagement with the tube T. The actuating cam 50 is rotatably mounted to the housing 28 and has a plurality of circumferentially-spaced peripheral cam surfaces 50A each engaged with one of the arms 46. Rotation of the cam 50 revolves its cam surfaces 50A and concurrently radially moves the arms 46 outwardly or permits the arms to be moved inwardly by the springs 48 and concurrently move tube support rollers 44 away from or toward the tube T to adjust their radial positions to accommodate any diameter size tube coaxially along the common centerline C. A lever 54 is attached to the cam 50 for use in manually rotatably moving the cam.

Referring now to FIGS. 8 to 21, each of the receptacles 26 of the dimension and flaw inspection stations 14A, 14B is formed by interconnected pairs of end walls 26A and side walls 26B and a bottom wall 26C and is open at the top. The interconnected walls of the receptacle 26 define a cavity 56 capable of holding a quantity of an energy coupling liquid, such as water. As will be described in detail later and in accordance with the invention of the above cross-referenced application, the side walls 26B of the receptacle 26 mounts the tube parameter measuring means 16 which preferably are in the form of first and second ultrasonic transducer assemblies 58, 60. The end walls 26A of the receptacle 26 have a pair of opposite openings 62 which communicate with the cavity 56 for receiving and passing the tube T therethrough such that the various tube parameters of interest can be measured by the transducer assemblies 58, 60 as the tube passes through the cavity 56 and the coupling liquid contained therein.

The cavities 56 of the respective receptacles 26 are interconnected to one another at the openings 62 in the end walls 26A of the receptacles 26 by the central passages 40 of the tube guide stand housings 28 so as to permit the tube T to pass through the serial arrangement 14 of inspection stations 14A, 14B along the common centerline C. Annular seals 64, such as O-rings, are provided about the openings 62 and between the tube guide stand 24 of one inspection station and the receptacle 26 of the next adjacent inspection station to inhibit leakage of coupling liquid from between the stations. The interconnection between the inspection stations 14A, 14B which permits passage of the tube also permits communication of some of the coupling liquid from one receptacle 26 to the next. For proper operation of the transducer assemblies 58, 60, the coupling liquid is required to be maintained at a certain minimum level in the receptacle cavities 56. The entry and exit liquid level control stations 18, 20 are operable to ensure fulfillment of this requirement.

Liquid Level Control Stations

Referring to FIGS. 26 to 37, the entry and exit liquid level control stations 18, 20 are disposed at the respective opposite ends of the serial arrangement 14 of inspection stations 14A, 14B. As briefly mentioned above, the control stations 18, 20 are operable for controlling the levels of energy coupling liquid, such as water, in the receptacle cavities 56 of the inspection stations 14A, 14B to ensure that the liquid levels remain above the minimum required for effective operation of the transducer assemblies 58, 60.

More particularly, each of the liquid level control stations 18, 20 includes a tank 66 and a liquid level regulating arrangement 68 coupled to each tank 66 for controlling the level of liquid therein and thereby in the receptacle cavities 56 of the inspection stations 14A, 14B. Each tank 66 is disposed at one of the opposite ends of the serial arrangement 14 of inspection stations 14A, 14B and interconnected in fluid flow communication with the respective inspection station at the one opposite end. Specifically, the entry liquid level control station 18 is interconnected to the first flaw inspection stations 14B via an additional tube guide stand 24A, as seen in FIGS. 1 to 3, 26 and 27. Also, each tank 66 has a chamber 70 for holding energy coupling liquid, such as water, and a pair of opposite inlet and outlet openings 72, 74 to the chamber 70 to permit passage of the tube T through the chamber.

Each liquid level regulating arrangement 68 of the control stations 18, 20 includes a plurality of dam and guide assemblies 76 mounted in the tank 66 and a pair of liquid inlet and outlet orifices 78, 80 on the tank 66 which communicate between the tank chamber 70 and an external water supply and drain. Each dam and guide assembly 76 is composed of a plate-like dam member 82 and a tube guide member 84. The dam member 82 has a recessed portion 82A along the middle of its upper edge providing a liquid overflow wier. The tube guide member 84 is composed of an annular bushing 86 mounted in a central opening 88 of the dam member 82 and an annular collar 90 attached to the dam member 82 adjacent the opening 88 for holding the bushing 86 in the opening 88. Bushings 86 of different opening sizes are provided and changed to accommodate different diameter sizes of tubes inspected. Alternative different dam members 82 can be provided matched with different tube diameter sizes so that changeover is accomplished merely by lifting out and replacing the dam members.

The interior surfaces of the bottom and sides of the tanks 66 have spaced grooves 92 defined therein which receive and support the plate-like dam members 82 in upright orientations so as to define a succession of liquid holding sections 70A, 70B, 70C, 70D of the tank chamber 70. The level of liquid in the outboard chamber section 70D communicates directly with the outlet orifice 80 and thus has a much lower level of liquid than in the other chamber sections 70A, 70B, 70C. Liquid flows from the inlet orifice 78 directly into the inboard chamber section 70A and then over the upper overflow portions 82A of the dam members 82 and through the intermediate chamber sections 70B, 70C to the outboard chamber section 70D. In such manner the liquid is maintained in the chamber sections 70A, 70B, 70C and thereby in the receptacles 26 at a more or less constant level above the minimum level required.

Tube Drives

As seen generally in FIGS. 1 to 3, the tube drives 22 are disposed adjacent to and outboard of the entry and exit liquid level control stations 18, 20 at the opposite ends of the serial arrangement 14 of inspection stations 14A, 14B. The tube drives 22 are operable for driving tubes T through the inspection and level control stations and, together with the tube guide stands 24, maintain the tube in coaxial alignment along the common centerline C irrespective of which tube diameter size is being inspected. The tube drives 22 are spaced from one another through a distance less than the length of the tube being inspected so that at least one of the drives 22 is engaged with the tube at all times.

The construction of each of the tube drives 22 preferably is substantially the same as the one disclosed in U.S. Pat. No. 4,735,541 to Clarence D. John, Jr., assigned to the same assignee as the present invention. The disclosure of that patent is incorporated herein by reference, and to obtain a greater understanding of the details of the tube drives 22, attention is directed to that patent.

Tube Parameter Measuring Means

Referring now to FIGS. 8 to 25, the tube parameter measuring means 16 in the form of first and second ultrasonic transducer assemblies 58, 60 are associated with the receptacle 26 of each of the inspection stations 14A, 14B. The transducer assemblies 58, 60 are supported in the proper predetermined orientation which matches the respective diameter size of the particular tube to be inspected at the respective inspection station. The provision of different ultrasonic transducer assemblies 58, 60 for different tube diameter sizes avoids the need for carrying out time-consuming readjustments whenever the diameter size of the tube being inspected is changed. All that the operator is required to do with respect to the changeover of transducer assemblies is to switch out, or electrically disconnect, the transducer assemblies which match the diameter sizes of tubes not being inspected and to switch in, or electrically connect, the transducer assemblies which match the diameter size of the tubes to be inspected next.

The first and second transducer assemblies 58, 60 each includes an ultrasonic transducer 94, 96 operable for sending out ultrasound waves and picking up the echo of such waves. At the tube dimension inspection station 14A, the pair of transducers 94 of the first transducer assemblies 58 respectively read the tube diameter and wall thickness, whereas the single transducer 96 of the second transducer assembly 60 is for calibration purposes. At each of the tube flaw inspection stations 14B, the pair of transducers 94 of the first transducer assemblies 58 respectively inspect for longitudinal flaws which typically take the form of lengthwise scratches found on the inside diameter surface of the tube. The transducers 94 are oriented to point in orthogonal relation to the tube but offset from the centerline of the tube, at an angle of incidence either above or below the centerline C. The pair of transducers 96 of the second transducer assemblies 60 respectively inspect for transverse flaws which typically take the form of circumferential scratches found on the outside diameter surface of the tube. The transducers 96 are oriented to point at small acute angles to the tube toward the centerline of the tube.

In accordance with the invention of the cross-referenced application, the first and second transducer assemblies 58, 60 are mounted to the side walls 26B of the receptacles 26 at the inspection stations 14A, 14B. The side walls 26B have first and second pairs 98, 100 of interconnected transverse and longitudinal bores 102, 104 and 106, 108 for respectively receiving the transducers 94, 96 and mounting members 110, 112 of the first and second transducer assemblies 58, 60. The mounting members 110, 112 either mount the transducers or hold them in the desired orientation. The transverse bores 102, 106 of the first and second pairs 98, 100, which receive the transducers 94, 96, extend between and open at the interior and exterior surfaces of the side walls 26B. The longitudinal bores 104, 108 of the first and second pairs 98, 100, which receive the mounting members 110, 112, extend vertically within the side walls 26B and open at the upper surface of the side walls and into the respective transverse bores 102, 106.

Referring to FIGS. 9, 12, 13, 19 and 20, the transverse bores 102, which receive the transducers 94 of the first transducer assemblies 58 that inspect for longitudinal flaws, are oblong in cross sectional shape to permit vertical adjustment of the transducers 94 to the desired position either above or below the centerline of the tube. On the other hand, the transverse bores 106, which receive the transducers 96 of the second transducer assemblies 60 that inspect for transverse flaws, are substantially the same cylindrical shape as the transducers 96 and are formed through the side walls 26B so as to be in the desired alignment with the centerline C and thereby with the tube extending through the receptacles 26 of the inspection stations 14B. Therefore, adjustment of the transducers 96 is neither required nor permitted.

Referring to FIGS. 12, 19, 22 and 23, the mounting members 110 of the first transducer assemblies 58 each include a mounting cylinder 114 having a transverse opening 116 for insertion of the transducer 94 and a central passage 118 leading from the upper side of the opening 116 to the upper end of the cylinder 114. The cylinder 114 is externally threaded at its upper end portion 114A and its central passage 118 is internally threaded at the lower end 118A. Also, the externally threaded upper end portion 114A of the cylinder 114 is reduced in outside diameter to provide an annulus 120 between the inside diameter of the longitudinal bore 104 in the receptacle side wall 26B and the outside diameter of the externally threaded upper portion 114A of the mounting cylinder 114.

Referring to FIGS. 12, 19 and 22 to 25, the mounting members 110 of the first transducer assemblies 58 also include main set screws 122, internally-threaded end caps 124, assist springs 125, retainer plate 126 and auxiliary set screws 128. Each main set screw 122 threads into the internally threaded lower end 118A of the central passage 118 of the one mounting cylinder 114 and engages the transducer 94 to retain it in the transverse opening 116 of the mounting cylinder 114. Each end cap 124 is threaded on the externally-threaded upper end portion 114A of the mounting cylinder 114 and extends into the annulus 120. Rotation of the end cap 124 produces axial movement of the mounting cylinder 114 within the longitudinal bore 104 to position the transducer 94 within the transverse bore 102. Spring 125 located between the bottom of the longitudinal bore 104 and the bottom of the mounting cylinder 114 assists in repositioning of the cylinder 114 upon rotation of the end cap 124. The end cap 124 has a peripheral groove 130 into which the edge of the retainer plate 126 extends. When adjustment of the end cap 124 is accomplished, the retainer plate 126 is tightened by screws 132 to the top surface of the receptacle side wall 26B so as to clamp and hold the end cap 124 in a stationary position against further rotation. The auxiliary set screws 128 are threaded through the side wall 26B from the exterior thereof to further engage and hold the mounting cylinder 114 against inadvertent rotation.

Figure 19:
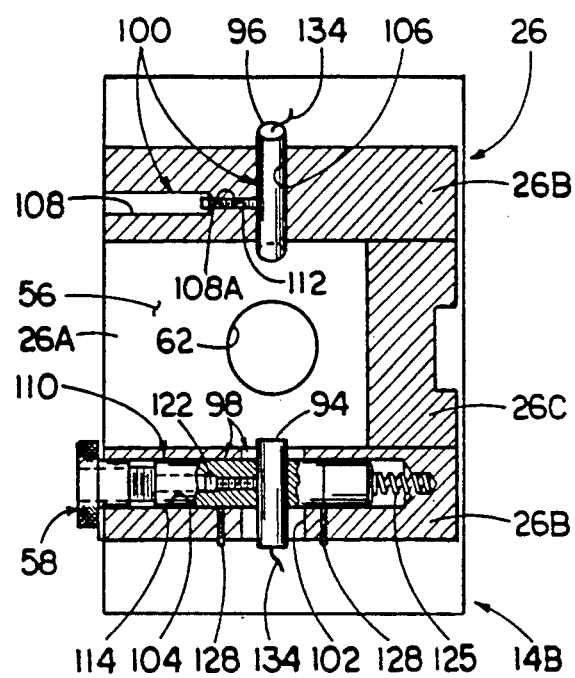
FIG. 19 is a cross sectional view of the receptacle and arrangement of transducer assemblies taken along line 19—19 of FIG. 18.
Figure 20:
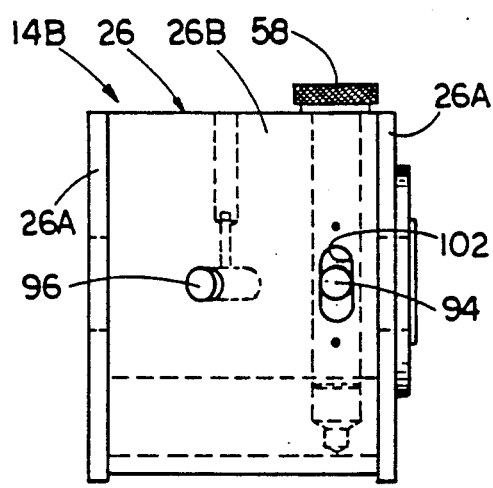
FIG. 20 is a side elevational view of the receptacle and arrangement of transducer assemblies as seen along line 20—20 of FIG. 18.
Figure 21:
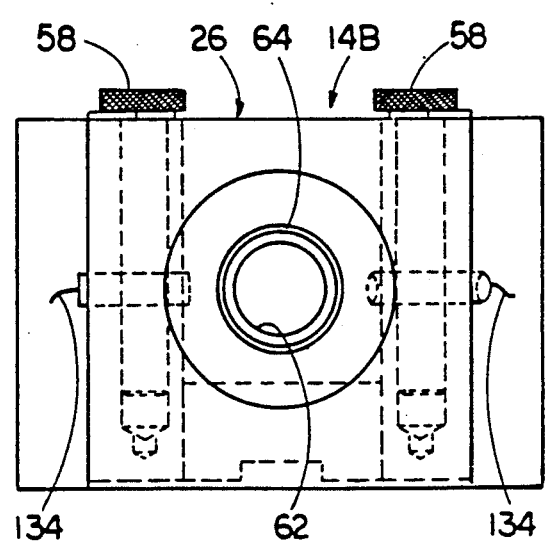
FIG. 21 is an end elevational view of the receptacle and arrangement of transducer assemblies as seen along line 21—21 of FIG. 20.
Figure 26:
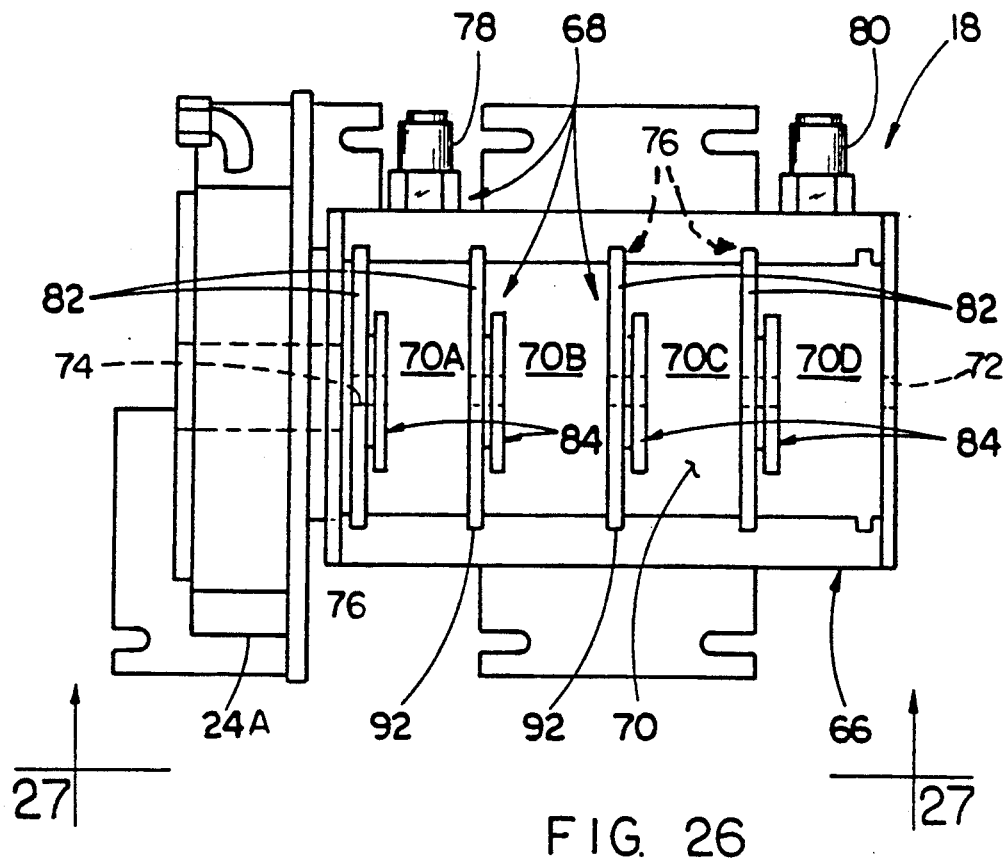
FIG. 26 is an enlarged top plan view of the entry liquid level control station and one of the tube guide stands of the tube inspection system.
Figure 27:
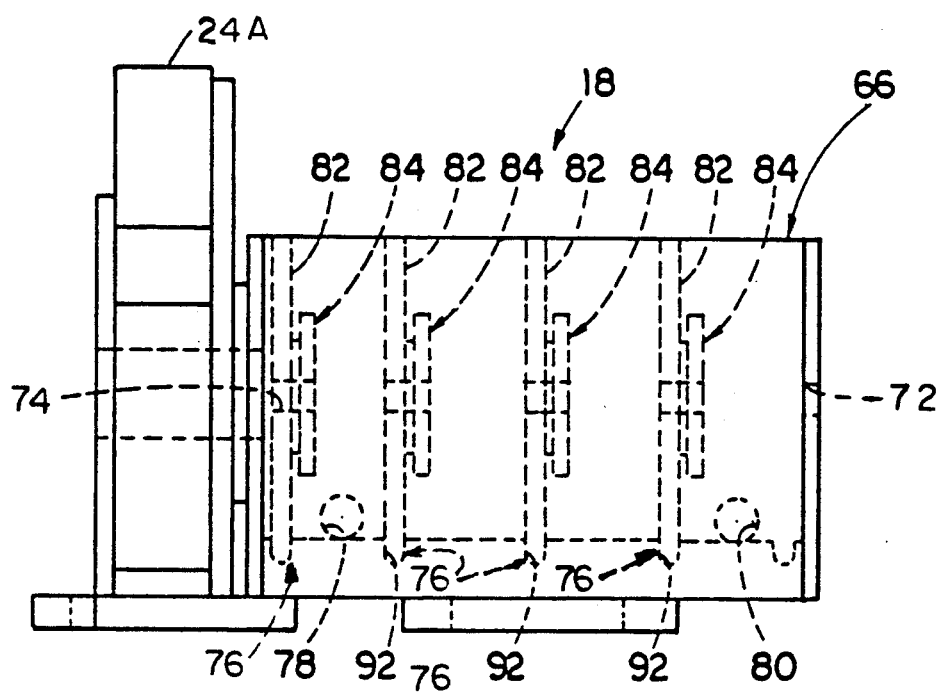
FIG. 27 is a side elevational view of the entry liquid level control station and one tube guide stand as seen along line 27—27 of FIG. 26.
Figure 28:
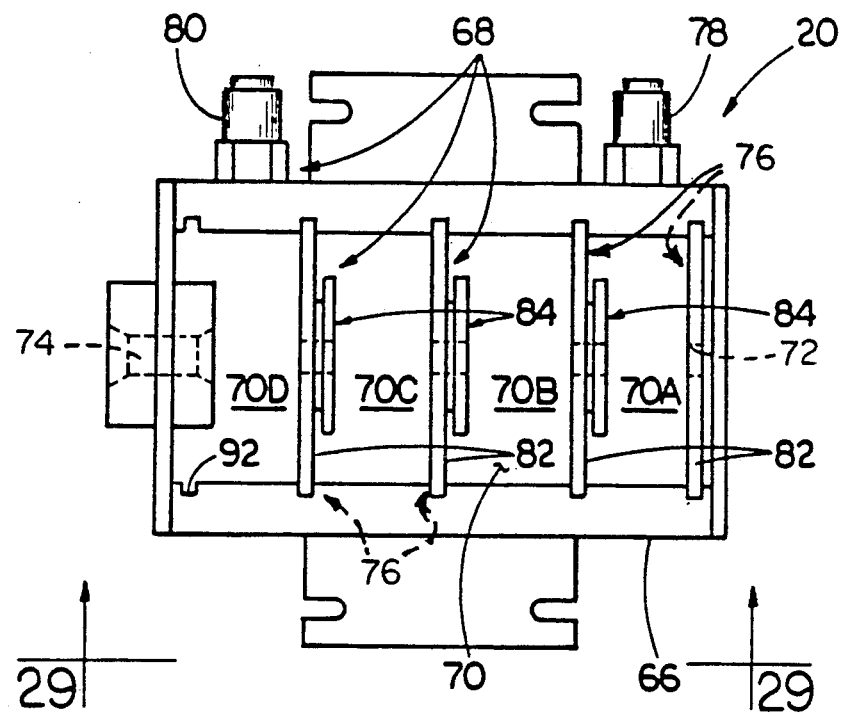
FIG. 28 is an enlarged top plan view of the exit liquid level control station of the tube inspection system.
Figure 29:
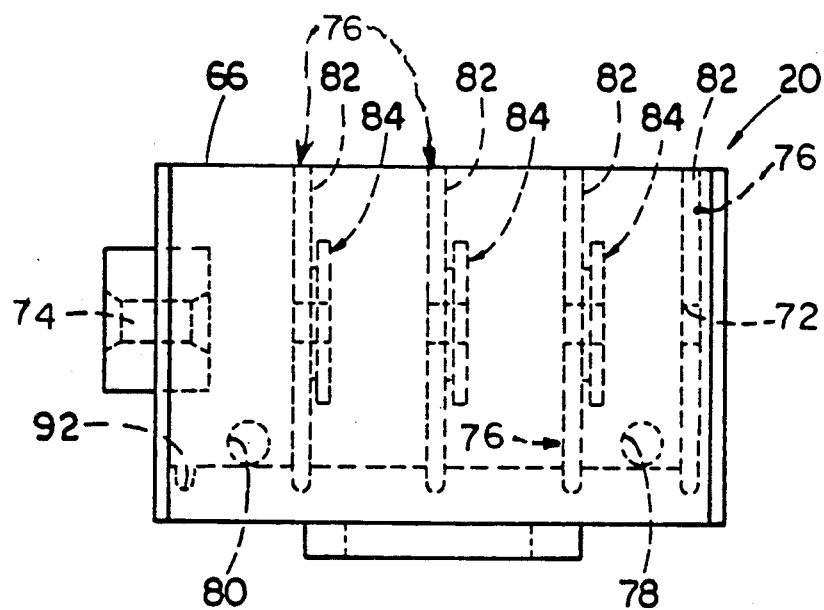
FIG. 29 is a side elevational view of the exit liquid level control station of the tube inspection system as seen along line 29—29 of FIG. 28.
Figure 35:
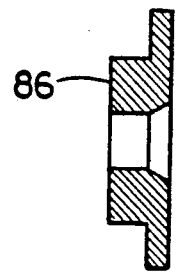
FIG. 35 is a cross-sectional view of the bushing taken along line 35—35 of FIG. 34.
Figure 34:
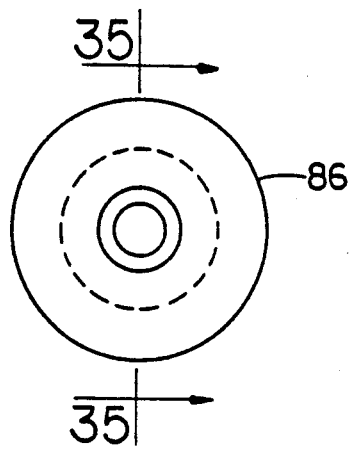
FIG. 34 is an enlarged side elevational view of a bushing of the dam and guide assembly of FIG. 31.
Figure 31:
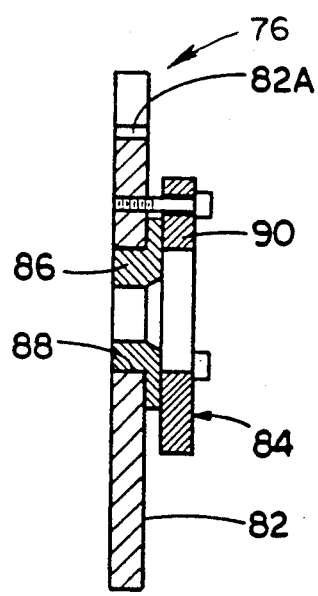
FIG. 31 is a cross-sectional view of the dam and guide assembly taken along line 31—31 of FIG. 30.
Figure 30:
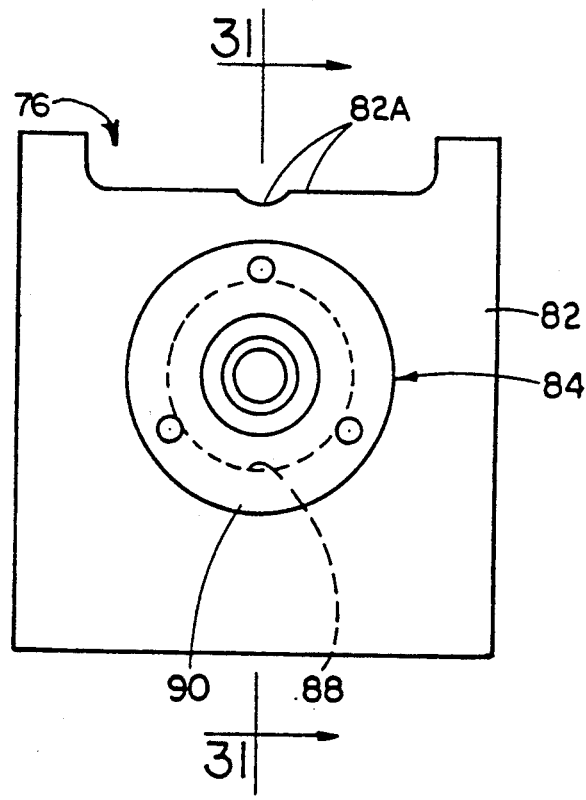
FIG. 30 is an end elevational view of one of a plurality of dam and guide assemblies composed of one dam member and one tube guide member and employed by the entry and exit liquid level control stations of FIGS. 26 and 28.
Figure 33:
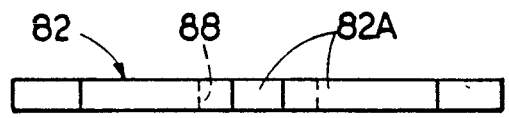
FIG. 33 is a top plan view of the dam member as seen along line 33—33 of FIG. 32.
Figure 32:
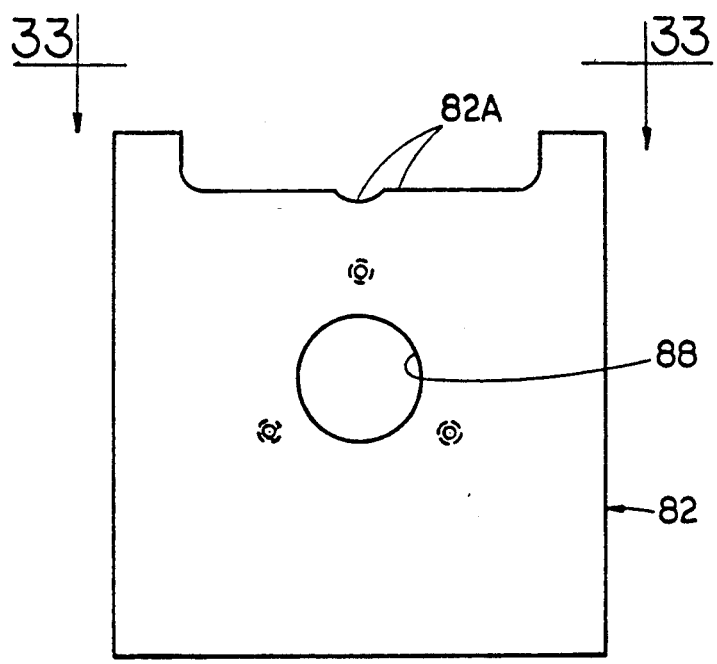
FIG. 32 is an end elevational view of one of a plurality of dam members employed by the entry and exit liquid level control stations of FIGS. 26 and 28.
Figure 36:
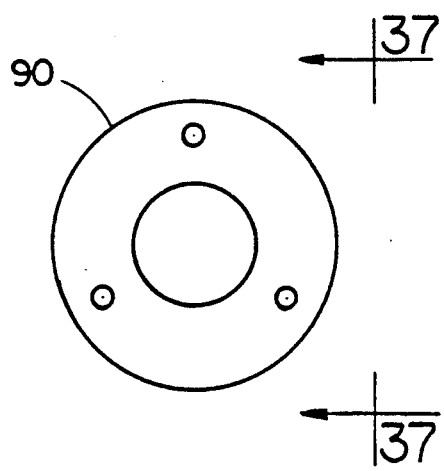
FIG. 36 is a side elevational view of a collar of the dam and guide assembly of FIG. 31.
Figure 37:
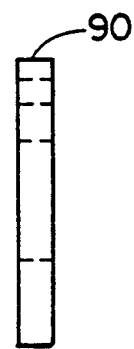
FIG. 37 is an end elevational view of the collar as seen along line 37—37 of FIG. 36.

As readily apparent in FIGS. 12 and 19, the construction of the mounting members 112 of the second transducer assemblies 60 for anchoring the transducers 96 in place is much simpler than in the case of mounting members 110 of the first transducer assemblies 58 for the transducers 94, as just described above. The mounting members 112 merely are set screws which thread into the lower ends 108A of the longitudinal bores 108 and engage the transducers 96. Furthermore, it is readily apparent in FIGS. 11, 12, 14, 18, 19 and 21 that by the transverse bores 102, 106 being open at the exterior surfaces of the receptacle side walls 26B, signal conductors 134 are easily attached to transducers 94, 96 without contacting the liquid in the receptacles.

Although not shown in the drawings, a proximity sensor can be associated with each inspection station 14A, 14B. The proximity sensor provides sensing and timing devices to alert the transducers 94, 96 as to when a tube has arrived in the transducer's range for inspection and when the tube has left that range. The advantage of using the proximity sensors is that they turn on and off the transducers while in range so that the transducers will not interpret the ends of the tubes as defects.

It is thought that the present invention and many of its attendant advantages will be understood from the foregoing description and it will be apparent that various changes may be made in the form, construction and arrangement of the parts of the invention described herein without departing from the spirit and scope of the invention or sacrificing all of its material advantages, the forms hereinbefore described being merely preferred or exemplary embodiments thereof.

We claim:

1. An ultrasonic tube inspection system capable of rapid changeover for inspecting tubes of different diameters, said inspection system comprising:
   (a) a serial arrangement of multiple separate inspection stations corresponding to different tube diameter sizes to be inspected, each inspection station being capable of inspecting tubes of a given one of different tube diameter sizes; and
   (b) tube parameter measuring means supported at each of said stations in an predetermined orientation corresponding to the given one diameter size of a tube to be inspected at said respective station;
   (c) each of said inspection stations including a receptacle defining a cavity for holding a quantity of energy coupling liquid and mounting said tube parameter measuring means;
   (d) each of said receptacles having a pair of opposite openings to said cavity for receiving and passing a tube therethrough such that the parameters of tube can be measured by said tube parameter measuring means as the tube passes through said cavity;
   (e) each of said stations also including means for guiding a tube through said receptacle cavity, said tube guiding means having a housing with a central passage for receiving and passing the tube therethrough;
   (f) said cavities of said receptacles being interconnected in liquid flow relationship with one another by said opposite openings of each of said receptacles and said central passage of said housing of each said tube guiding means.

2. The inspection system as recited in claim 1, wherein said serial arrangement of inspection stations includes one tube dimension inspection station for inspecting tubes irrespective of their diameter sizes.

3. The inspection system as recited in claim 1, wherein said serial arrangement of inspection stations includes a plurality of tube flaw inspection stations each for inspecting tubes of the given one of the different diameter sizes.

4. The inspection system as recited in claim 1, wherein each said tube guiding means supports said receptacle disposed at the same inspection station.

5. The inspection system as recited in claim 1 wherein said tube guiding means further includes:
   a self-centering mechanism mounted to said housing and aligned with said passage thereof for guiding the tube through said passage and said receptacle cavity along a common centerline irrespective of which tube diameter size is being inspected.

6. The inspection system as recited in claim 5, wherein said self-centering mechanism includes:
   a plurality of tube support elements;
   a plurality of arms movably mounted to said housing in radial relation to said common centerline and in spaced relation to one another circumferentially about said common centerline, each of said arms mounting one of said tube support elements at an inner end of said arm such that said elements are arranged in spaced circumferential relation about the tube aligned along said common centerline; and
   positioning means mounted to said housing for engaging each of said arms and being operable for concurrently radially moving said arms and thereby said tube support elements toward and away from the tube to permit positioning of any diameter size tube coaxially along said common centerline.

7. The inspection system as recited in claim 6, wherein each of said tube support elements is a roller rotatably mounted at said inner end of said arm.

8. The inspection system as recited in claim 1, wherein said housing of each tube guiding means supports said receptacle disposed at the same station.

9. The inspection system as recited in claim 1, wherein said tube parameter measuring means includes a plurality of ultrasonic transducer assemblies.

10. An ultrasonic tube inspection system capable of rapid changeover for inspecting tubes of different diameters, said inspection system comprising:
    (a) a serial arrangement of multiple separate inspection stations corresponding to different tube diameter sizes to be inspected, each inspection station being capable of inspecting tubes of a given one of different tube diameter sizes; and
    (b) tube parameter measuring means supported at each of said stations in an predetermined orientation corresponding to the given one diameter size of a tube to be inspected at said respective station;
    (c) each of said inspection stations including a receptacle defining a cavity for holding a quantity of energy coupling liquid and mounting said tube parameter measuring means, each of said inspection stations also including means for guiding a tube through said receptacle cavity;
    (d) said tube guiding means including a housing having a central passage for receiving and passing the tube therethrough, said tube guiding means also including a self-centering mechanism mounted to said housing and aligned with said passage thereof for guiding the tube through said passage and receptacle cavity along a common centerline irrespective of which tube diameter size is being inspected;
    (e) said self-centering mechanism including a plurality of tube support elements and a plurality of arms movably mounted to said housing in radial relation to said common centerline and in spaced relation to one another circumferentially about said common centerline, each of said arms mounting one of said tube support elements at an inner end of said arm such that said elements are arranged in spaced circumferential relation about the tube aligned along said common centerline, said self-centering means also including positioning means mounted to said housing for engaging each of said arms and being operable for concurrently radially moving said arms and thereby said tube support elements toward and away from the tube to permit positioning of any diameter size tube coaxially along said common centerline;
    (f) said positioning means including means mounted to said housing and engaging each of said arms for biasing said arms to move toward said common centerline so as to maintain said tube support elements in engagement with the tube, said positioning means also including a cam rotatably mounted to said housing and having a plurality of peripheral cam surfaces each engaged with one of said arms such that upon rotation of said cam said cams surfaces thereof control radial movement of said arms and tube support elements therewith.

11. The inspection system as recited in claim 10, further comprising:
    a lever attached to said cam for use in rotatably moving said cam.

12. An ultrasonic tube inspection system capable of rapid changeover for inspecting tubes of different diameters, said inspection system comprising:
    (a) a serial arrangement of multiple separate inspection stations corresponding to different tube diameter sizes to be inspected, each inspection station being capable of inspecting tubes of a given one of different tube diameter sizes; and
    (b) tube parameter measuring means supported at each of said stations in an predetermined orientation corresponding to the given one diameter size of a tube to be inspected at said respective station;
    (c) each of said inspection stations including a receptacle defining a cavity for holding a quantity of energy coupling liquid and mounting said tube parameter measuring means, said receptacle having a pair of opposite openings to said cavity for receiving and passing a tube therethrough such that the parameters of tube can be measured by said tube parameter measuring means as the tube passes through said cavity;
    (d) each of said inspection stations also including means for guiding a tube through said receptacle cavity, said tube guiding means including a housing with a central passage for receiving and passing the tube therethrough and a self-centering mechanism mounted on said housing and aligned with said passage for guiding the tube through said passage and through said receptacle cavity and opposite openings along a common centerline irrespective of which tube diameter size is being inspected;
    (e) said self-centering mechanism including a plurality of tube support rollers and a plurality of arms movably mounted to said housing in radial relation to said common centerline and in spaced relation to one another circumferentially about said common centerline, each of said arms mounting one of said tube support rollers at an inner end of said arm such that said rollers are arranged in spaced circumferential relation about a tube aligned along said common centerline, said self-centering mechanism also including positioning means mounted to said housing for engaging each of said arms and being operable for concurrently radially moving said arms and thereby said tube support rollers toward and away from the tube to permit positioning of any diameter size tube coaxially along said common centerline;

(f) said positioning means including means mounted to said housing and engaging each of said arms for biasing said arms to move toward said common centerline so as to maintain said tube support rollers in engagement with the tube, said positioning means also including a cam rotatably mounted to said housing and having a plurality of peripheral cam surfaces each engaged with one of said arms such that upon rotation of said cam said cams surfaces control radial movement of said arms and tube support rollers therewith.

13. A tube inspection system capable of rapid changeover for inspecting tubes of different diameters sizes, said inspection system comprising;
(a) a serial arrangement of multiple separate inspection stations corresponding to different tube diameter sizes to be inspected and containing an energy coupling liquid, each inspection station being capable of inspecting tubes of a given one of different tube diameter sizes;
(b) means supported at each of said inspection stations for inspecting the tubes of the given one of the different diameter sizes; and
(c) entry and exit liquid level control stations disposed at respective opposite ends of said serial arrangement of inspection stations for controlling the liquid level in the inspection stations, each of said liquid level control stations including a tank connected in liquid flow communication with and disposed at one of said opposite ends of said serial arrangement of inspection stations and a liquid level regulating arrangement coupled to said tank for controlling the level of liquid in said tank and thereby in said inspection stations;
(d) each said tank including a chamber for holding energy coupling liquid and a pair of opposite inlet and outlet openings to said chamber to permit passage of a tube through said chamber;
(e) each said liquid level regulating arrangement including at least one dam and guide assembly mounted in said chamber of said tank and liquid inlet and outlet orifices connected on said tank in flow communication with chamber thereof.

14. The inspection system as recited in claim 13, wherein each dam and guide assembly includes:
a dam member having an upper liquid overflow portion; and
a tube guide member mounted to a central opening of said dam member and defining an opening through which a tube extends in passing through said respective liquid level control station.

15. A tube inspection system capable of rapid changeover for inspecting tubes of different diameter sizes, said inspection system comprising:
(a) a serial arrangement of multiple separate inspection stations corresponding to different tube diameter sizes to be inspected and containing an energy coupling liquid, each inspection station being capable of inspecting tubes of a given one of different tube diameter sizes;
(b) tube parameter measuring means supported at each of said stations in a proper orientation corresponding to the given one diameter size of a tube to be inspected at the respective station;
(c) means disposed at opposite ends of the serial arrangement of stations for controlling the level of the liquid in the stations; and
(d) means disposed adjacent to liquid level controlling means at each opposite end of the serial arrangement of stations for driving tubes through the stations aligned along a common centerline irrespective of which tube diameter size is being inspected;
(e) each of said inspection stations including a receptacle defining a cavity for holding a quantity of energy coupling liquid and mounting said tube parameter measuring means;
(f) each of said receptacles having a pair of opposite openings to said cavity for receiving and passing a tube therethrough such that the parameters of the tube can be measured by said tube parameter measuring means as the tube passes through said receptacle;
(g) each of said stations also including means for guiding a tube through said receptacle cavity, said tube guiding means including a housing having a central passage for receiving and passing the tube therethrough and a self-centering mechanism mounted in the housing and aligned with said passage for guiding the tube through said passage and through said receptacle cavity and openings along the common centerline irrespective of which tube diameter size is being inspected;
(h) said cavities of said receptacles being interconnected in liquid flow relationship with one another by said opposite openings of each said receptacle and said central passage of said housing of each said tube guiding means.

16. The inspection system as recited in claim 15, wherein said serial arrangement of inspection stations includes one tube dimension inspection stations for inspecting tubes irrespective of their diameter sizes.

17. The inspection system as recited in claim 15, wherein said serial arrangement of inspection stations includes a plurality of tube flaw inspection stations each for inspecting tubes of the given one of the different tube diameter sizes.

18. The inspection system as recited in claim 15, wherein said housing of each tube guiding means supports disposed at the same station.

19. The inspection system as recited in claim 15, wherein liquid level controlling means includes:
a pair of tanks each connected in liquid flow communication with and disposed at one of said opposite ends of said serial arrangement of inspection stations; and
a pair of liquid level regulating arrangements each coupled to one of said tanks for controlling the level of liquid in said tank and thereby in said inspection stations.

20. The inspection system as recited in claim 15, wherein said tube parameter measuring means includes a plurality of ultrasonic transducer assemblies.

21. A tube inspection system capable of rapid changeover for inspecting tubes of different diameter sizes, said inspection system comprising:
(a) a serial arrangement of multiple separate inspection stations corresponding to different tube diameter sizes to be inspected and containing an energy coupling liquid, each inspection station being capable of inspecting tubes of a given one of different tube diameter sizes;

(b) tube parameter measuring means supported at each of said stations in a proper orientation corresponding to the given one diameter size of a tube to be inspected at the respective station;

(c) means disposed at opposite ends of the serial arrangement of stations for controlling the level of the liquid in the stations; and (d) means disposed adjacent to liquid level controlling means at each opposite end of the serial arrangement of stations for driving tubes through the stations aligned along a common centerline irrespective of which tube diameter size is being inspected;

(e) said liquid level controlling means including a pair of tanks each connected in liquid flow communication with and disposed at one of said opposite ends of said serial arrangement of inspection stations, said liquid level controlling means also including a pair of liquid level regulating arrangements each coupled to one of said tanks for controlling the level of liquid in said tank and thereby in said inspection stations;

(f) each said tank including a chamber for holding energy coupling liquid and a pair of opposite inlet and outlet openings to said chamber to permit passage of a tube through said chamber;

(g) each said liquid level regulating arrangement including a plurality of dam and guide assemblies mounted in said chamber of each respective tank and liquid inlet and outlet orifices connected on said tank in flow communication with chamber thereof.

22. The inspection system as recited in claim 21, wherein each dam and guide assembly includes:

a dam member having an upper liquid overflow portion; and a tube guide member mounted to a central opening of said dam member and defining an opening through which a tube extends in passing through said respective liquid level control station.

23. An ultrasonic tube inspection system capable of rapid changeover for inspecting tubes of different diameter sizes, said inspection system comprising;

(a) a serial arrangement of multiple separate inspection stations corresponding to different tube diameter sizes to be inspected, each inspection station being capable of inspecting tubes of a given one of different tube diameter sizes, each of said stations including a receptacle and a tube guiding means, said receptacle having a cavity for holding an ultrasonic energy transmitting liquid and a pair of opposite openings to said cavity for receiving a tube therethrough, each of said tube guiding means including a housing having a central passage for receiving a tube therethrough and a self-centering mechanism mounted in said housing for guiding the tube through said passage and through said receptacle cavity and openings along a common centerline irrespective of which tube diameter size is being inspected, said cavities of said receptacles being interconnected in fluid flow relationship with one another through said openings of said receptacles and said central passages of said tube guiding means by which the tubes pass through said serial arrangement of separate inspection stations;

(b) first and second ultrasonic transducer assemblies supported by said receptacle at each of said stations in a proper orientation to match the given one diameter size of a tube to be inspected at said respective station;

(c) means disposed at opposite ends of said serial arrangement of separate inspection stations for controlling the level of the liquid in said stations, said level controlling means including a pair of tanks and a liquid flow regulating arrangement coupled to each tank for controlling the level of liquid in each tank and thereby in said cavity of said receptacle of each of said stations, each tank being disposed at one of said opposite ends of said serial arrangement of stations and interconnected in fluid flow communication with said one opposite end thereof, each of said tanks having a chamber for holding liquid and a pair of opposite inlet and outlet openings to said chamber to permit passage of the tube through said chamber; and (d) means disposed adjacent to said water level controlling means at each opposite end of said serial arrangement of stations for driving tubes through said stations also aligned along the common centerline irrespective of which tube diameter size is being inspected.

24. The inspection system as recited in claim 23, wherein said serial arrangement of inspection stations includes one tube dimension inspection station for inspecting tubes irrespective of their diameter sizes.

25. The inspection system as recited in claim 23, wherein said serial arrangement of inspection stations includes a plurality of tube flaw inspection stations each for inspecting tubes of the given one of the different tube diameter sizes.

* * * * *